United States Patent
Suzuki et al.

(10) Patent No.: US 12,115,352 B2
(45) Date of Patent: Oct. 15, 2024

(54) NEEDLELESS INJECTOR

(71) Applicant: DAICEL CORPORATION, Osaka (JP)

(72) Inventors: Takamasa Suzuki, Tokyo (JP); Yuzo Yamamoto, Tokyo (JP); Yuko Sakaguchi, Tokyo (JP)

(73) Assignee: DAICEL CORPORATION, Osaka (JP)

( * ) Notice: Subject to any disclaimer, the term of this patent is extended or adjusted under 35 U.S.C. 154(b) by 896 days.

(21) Appl. No.: 17/263,310

(22) PCT Filed: Aug. 2, 2019

(86) PCT No.: PCT/JP2019/030523
§ 371 (c)(1),
(2) Date: Jan. 26, 2021

(87) PCT Pub. No.: WO2020/027325
PCT Pub. Date: Feb. 6, 2020

(65) Prior Publication Data
US 2021/0162131 A1    Jun. 3, 2021

(30) Foreign Application Priority Data
Aug. 3, 2018 (JP) ................. 2018-146758

(51) Int. Cl.
*A61M 5/30* (2006.01)
*A61M 5/315* (2006.01)

(52) U.S. Cl.
CPC .............. *A61M 5/30* (2013.01); *A61M 5/315* (2013.01)

(58) Field of Classification Search
CPC ............................. A61M 5/30; A61M 5/3007
See application file for complete search history.

(56) References Cited

U.S. PATENT DOCUMENTS 6,406,456 B1   6/2002   Slate et al.
6,645,169 B1   11/2003   Slate et al.
(Continued)

FOREIGN PATENT DOCUMENTS

JP     11-309211 A    11/1999
JP     2002-95748 A    4/2002
(Continued)

OTHER PUBLICATIONS

Extended European Search Report for European Application No. 19843108.2, dated Apr. 8, 2022.
(Continued)

*Primary Examiner* — Dung T Ulsh
(74) *Attorney, Agent, or Firm* — Birch, Stewart, Kolasch & Birch, LLP (57) ABSTRACT

A needleless injector configured to inject an injection intended substance to an injection target region, by injecting the injection intended substance includes a nozzle portion and a pressing portion, and a predetermined gap is formed between the nozzle portion and the pressing portion. The nozzle portion is formed to have a portion of the distal end portion that comes into contact with the injection target region and has a width (a) falling within a range from 3.5 mm to 5.5 mm, and a ratio (b/a) defined by an inner diameter (b) of a portion of a distal end portion of the pressing portion that comes into contact with the injection target region by the width (a) falls within a range from 1.5 to 5.0. A part of the injection target region is received in the predetermined gap when the pressing portion presses the injection target region.

4 Claims, 9 Drawing Sheets

(56) References Cited

U.S. PATENT DOCUMENTS

| | | |
|---|---|---|
| 2002/0151842 A1 | 10/2002 | Gonnelli et al. |
| 2002/0156418 A1 | 10/2002 | Gonnelli et al. |
| 2002/0161329 A1 | 10/2002 | Gonnelli et al. |
| 2009/0137949 A1 | 5/2009 | Landau et al. |
| 2010/0025503 A1 | 2/2010 | Williamson |
| 2010/0076374 A1 | 3/2010 | Landau et al. |
| 2011/0172634 A1 | 7/2011 | Gonnelli et al. |
| 2011/0275994 A1 | 11/2011 | Iwase et al. |
| 2011/0288521 A1 * | 11/2011 | Bingham ............... A61M 5/30 604/500 |
| 2014/0107578 A1 | 4/2014 | Iwase et al. |

FOREIGN PATENT DOCUMENTS

| | | | |
|---|---|---|---|
| JP | 2004-520884 A | 7/2004 | |
| JP | 2011-604765 A | 2/2011 | |
| JP | 5366195 B2 | 12/2013 | |
| JP | 2020-14530 A | 1/2020 | |
| WO | WO-02051470 A2 * | 7/2002 | ............. A61M 5/30 |
| WO | WO 2019/235598 A1 | 12/2019 | |

OTHER PUBLICATIONS

International Search Report issued Oct. 21, 2019, in PCT/JP2019/030523.
Written Opinion issued Oct. 21, 2019, in PCT/JP2019/030523.

* cited by examiner

NEEDLELESS INJECTOR

TECHNICAL FIELD

The present invention relates to a needleless injector that injects an injection intended substance to an injection target region without using an injection needle.

BACKGROUND ART

Needleless injectors that inject an injection solution without an injection needle when performing injection to a subject have been widely known. For example, Patent Document 1 discloses a needleless injector having a cylindrical skirt formed on its distal end side, and having an injection tube arranged in a compartment defined by the skirt. In such a needleless injector disclosed in Patent Document 1, a fluid medication is injected into a patient through a port of the injection tube, in a state where the injector is positioned with the port pressed against the skin of the patient. On the other hand, Patent Document 2 discloses a needleless injector having an injection tube arranged in a compartment defined by a skirt as described above, wherein air in the compartment is sucked by a suction pump in a state where an opening end of the skirt is pressed against the skin of the patient.

Patent Document 3 discloses a medication injection device including a needle tube having a needle point that can be tapped into an organism (living body), as well as an adjustment portion provided with the needle point of the needle tube and a cylindrical stabilizing portion that comes into contact with the skin when the needle tube is tapped into the organism. With this technique, for example, the distance from the portion of the stabilizing portion that comes into contact with the skin to the adjustment portion is set to be in a range of 4 mm to 15 mm. This prevents the stabilizing portion from hindering blistering of the affected area.

CITATION LIST

Patent Document

Patent Document 1: US 6,645,169
Patent Document 2: US 6,406,456
Patent Document 3: JP 5366195 B

SUMMARY OF INVENTION

Technical Problem

A needleless injector includes a nozzle portion having an injection port formed for injecting an injection intended substance. To precisely deliver the injection intended substance injected from the injection port to a target region in the injection target region with such a needleless injector, an appropriate contact state between the injection target region and the nozzle portion needs to be achieved and maintained while the injection intended substance is being injected to the target region. Such a contact state between the injection target region and the nozzle portion enabling precise delivery of the injection intended substance to the target region of the injection target region may be hereinafter referred to as a "desired contact state".

However, the contact state between the injection target region and the nozzle portion may vary due to a difference in a manipulation performed by a user and the like. Thus, the desired contact state may be difficult to achieve by the user simply pressing the nozzle portion against the surface of the injection target region.

The needleless injector described in Patent Document 1 has the cylindrical skirt formed around the port of the injection tube. Still, the position of the injector relative to the affected area is determined with the port pressed against the skin of the patient. Thus, the contact state between the port and the skin may vary due to a difference in the manipulation performed by the user and the like. With the technique disclosed in Patent Document 2, the contact state between the port of the injection tube and the skin of the patient is achieved with the pressure in the compartment reduced, and thus the skin of the patient is sucked into the compartment. Unfortunately, the desired contact state between the port and the skin cannot be achieved or maintained without a configuration for reducing the pressure in the compartment.

The adjustment portion and the stabilizing portion of the medication injection device according to Patent Document 3 are configurations for defining the position of the needle point of the needle tube to be tapped into the skin. Such a technique of an injector with a needle cannot be directly applied to needleless injectors.

In view of the problems described above, an object of the present invention is to provide a needleless injector with which a desired contact state can be appropriately achieved and maintained between the injection target region and the nozzle portion.

Solution to Problem

A needleless injector according to an embodiment of the present invention includes a nozzle portion and a pressing portion, and a predetermined gap is formed between the nozzle portion and the pressing portion. To achieve the object described above, in the needleless injector according to an embodiment of the present invention, a ratio (b/a) defined by dividing an inner diameter (b) of a portion of a distal end portion of the pressing portion that comes into contact with the injection target region by a width (a) of a portion of a distal end portion of the nozzle portion that comes into contact with the injection target region falls within a range from 1.5 to 5.0. A part of the injection target region is received in the predetermined gap when the pressing portion presses the injection target region. With this configuration, a desired contact state can be appropriately achieved and maintained between the injection target region and the nozzle portion.

More specifically, the needleless injector according to an embodiment of the present invention is a needleless injector configured to inject an injection intended substance to an injection target region without using an injection needle, by injecting the injection intended substance in a state where the injection target region is pressed, and includes a containing portion that is provided in a housing of the needleless injector, and is configured to contain the injection intended substance, a drive unit that is provided in the housing, and is configured to generate injection energy for injecting the injection intended substance contained in the containing portion, a nozzle portion that is provided to protrude from a predetermined end portion as a predetermined end portion of the housing on a side of the containing portion, has an injection port formed for injecting toward the injection target region, the injection intended substance provided with the injection energy generated by the drive unit, and is configured to have a distal end portion coming into contact with the injection target region when the injection intended substance is injected from the injection port, and a pressing portion that is provided to protrude from the predetermined end portion and to have a cylindrical shape to surround the nozzle portion with a predetermined gap formed between the nozzle portion and the pressing portion, and is configured to have a distal end portion coming into contact with the injection target region when the injection intended substance is injected from the injection port. The nozzle portion is formed to have a portion of the distal end portion that comes into contact with the injection target region and has a width (a) falling within a range from 3.5 mm to 5.5 mm, and the needleless injector according to an embodiment of the present invention is configured in such a manner that a ratio (b/a) defined by dividing an inner diameter (b) of a portion of the distal end portion of the pressing portion that comes into contact with the injection target region by the width (a) of the portion of the distal end portion of the nozzle portion that comes into contact with the injection target region falls within a range from 1.5 to 5.0, and that a part of the injection target region is received in the predetermined gap when the pressing portion presses the injection target region.

With the needleless injector according to an embodiment of the present invention, pressing of the injection target region by the pressing portion induces raising of a portion of the injection target region surrounded by the pressing portion toward the injector. In the needleless injector described above, the nozzle portion is provided to protrude from the predetermined end portion of the housing and to be surrounded by the pressing portion that presses the injection target region. Thus, when the injection target region is pressed by the pressing portion of the needleless injector according to an embodiment of the present invention, the region of the injection target region surrounded by the pressing portion is raised toward the injector to enter the predetermined gap, and is pressed against the distal end portion of the nozzle portion. The injection target region and the nozzle portion thus brought into contact with each other facilitates achieving and maintaining of a desired contact state between the injection target region and the nozzle portion.

When the ratio (b/a) falls below 1.5, the predetermined gap becomes narrow, rendering a space for the injection target region to deform as described above difficult to secure. When the ratio (b/a) is greater than 5.0, pressing of the injection target region by the pressing portion involves a higher risk of being affected by the shape of the injection target region. Thus, the pressing may fail to be evenly applied. If the desired contact state fails to be achieved and maintained between the injection target region and the nozzle portion when the injection intended substance is injected to the injection target region due to these factors, the injection intended substance may fail to be precisely delivered to the target region of the injection target region.

In view of this, the needleless injector according to the present invention is configured in such a manner that a ratio (b/a) defined by dividing an inner diameter (b) of a portion of a distal end portion of the pressing portion that comes into contact with the injection target region by a width (a) of a portion of a distal end portion of the nozzle portion that comes into contact with the injection target region falls within a range from 1.5 to 5.0. Preferably, (b/a) is 2.0 or greater and 4.5 or less. The width of the nozzle portion described above is a width in the injector as viewed in a vertical cross sectional view of the housing, and is a width of the distal end portion of the nozzle portion that comes into contact with the injection target region. With this configuration, the injection target region can be favorably risen into the predetermined gap, and the predetermined gap can suitably receive the injection target region thus deformed to be risen. Furthermore, in the needleless injector according to the present invention, the width (a) described above is set to be 3.5 or greater and 5.5 mm or less, whereby the distal end surface of the nozzle portion and the injection target region can stably be in contact with each other. With the needleless injector according to the present invention having the configuration described above, the desired contact state can be achieved between the injection target region and the nozzle portion. Furthermore, the desired contact state can be achieved and maintained even when the injection target region is tilted.

Furthermore, with the needleless injector according to the present invention, such a desired contact state may be stably achieved. This is because the geometric shapes of the pressing portion and the nozzle portion have a dominant impact on the mode of deformation of the injection target region described above. This means that the contact state between the injection target region and the nozzle portion is less likely to vary due to a difference in the manipulation by the user and the like. In addition, in the needleless injector described above, the nozzle portion is fixed by being surrounded by the injection target region received in the predetermined gap. This facilitates maintaining of the desired contact state achieved between the injection target region and the nozzle portion.

Thus, in the needleless injector described above, the desired contact state can be suitably achieved and maintained between the injection target region and the nozzle portion, whereby the administration of the injection intended substance to the target region of the injection target region can be accurately, stably, and reproducibly performed.

The pressing portion may have a tapered shape to have a distance between an inner circumferential surface and an outer circumferential surface of the pressing portion gradually decreasing toward a distal end side along an axial direction. With this configuration, the load applied to the injection target region by the pressing portion is concentrated. This makes it easier for a part of the injection target region to be received in the predetermined gap, and further facilitates the stable maintaining of the pressing state. Thus, the desired contact state can be stably achieved and maintained between the injection target region and the nozzle portion.

The nozzle portion may be formed to have a width gradually decreasing toward the distal end side. With this configuration, when the injection target region is pressed by the pressing portion and the injection target region deforms as described above, the deformed injection target region and the distal end portion of the nozzle portion can be more easily brought into close contact with each other. Then, the injection target region surrounds the distal end portion of the nozzle portion to be in close contact with the distal end portion, whereby the nozzle portion is easily fixed by the injection target region. As a result, maintaining of the desired contact state between the injection target region and the nozzle portion is facilitated.

Advantageous Effects of Invention

With the present invention, the desired contact state can be appropriately achieved and maintained between the injection target region and the nozzle portion.

DESCRIPTION OF EMBODIMENTS

With reference to the drawings, an injector according to an embodiment of the present invention will be described with a needleless injector 1 (hereinafter, simply referred to as "injector 1") without a needle used as an example. Note that configurations of the following embodiment are provided as examples, and the present invention is not limited to the configurations of the embodiment.

Embodiment

Figure 1:
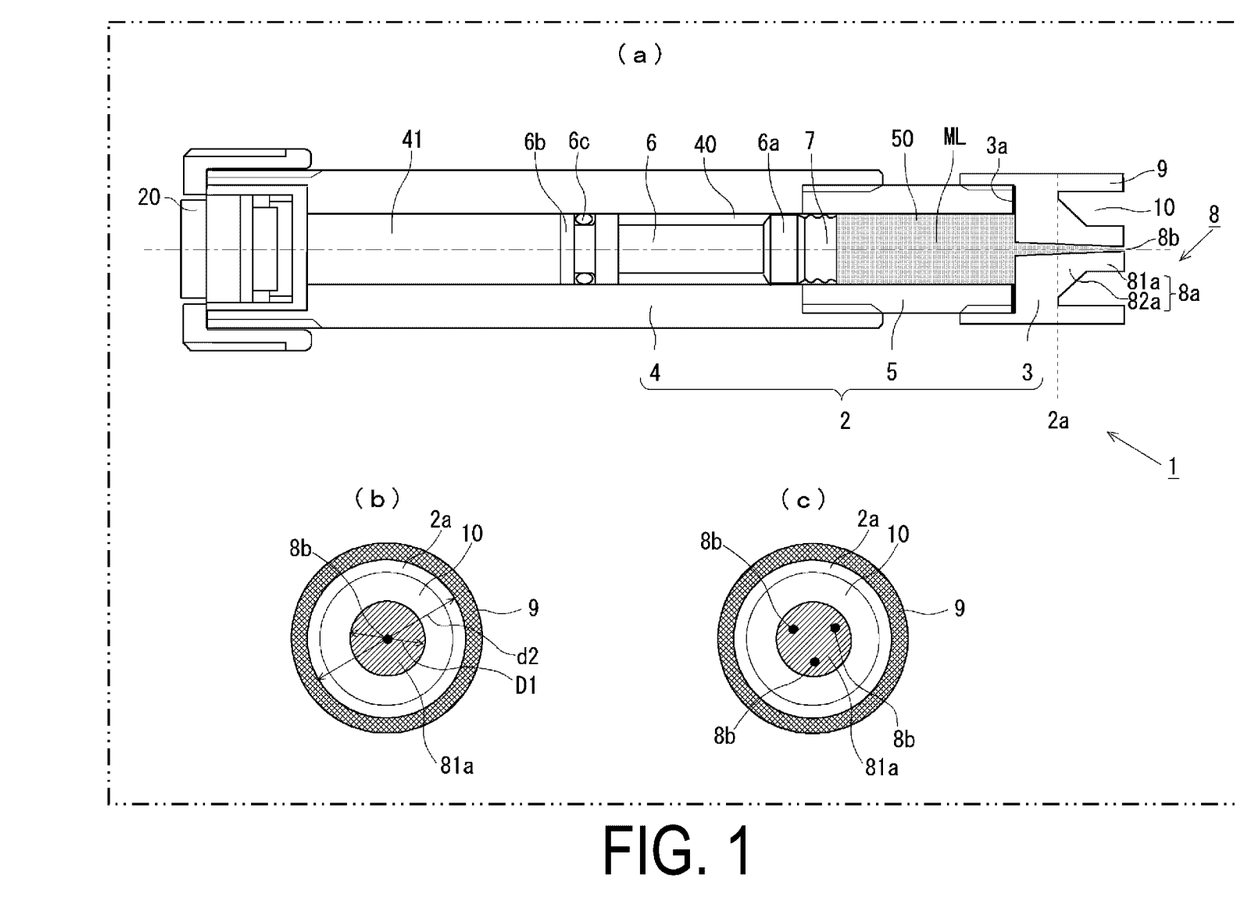
FIG. 1 is a view illustrating a schematic configuration of an injector according to an embodiment of the present invention.

FIG. 1(*a*) is a cross-sectional view of an injector 1, and FIGS. 1(*b*) and (*c*) are views of the injector 1 as viewed from the distal end side. Note that, in the following description of the present application, the injection intended substance injected into the injection target region of a subject using the injector 1 will be comprehensively referred to as "injection solution". However, this is not intended to limit the content and form of the injected substance. The injection intended substance may or may not have the components, to be delivered to a skin structure, dissolved. The injection intended substance is also not limited to a specific form, as long as it can be pressurized to be injected to the skin structure from an injection port. Thus, the injection intended substance may take various forms such as liquid, gel, or powder.

The injector 1 includes: a housing 2 including a distal end side housing 3, a proximal end side housing 4, and a syringe portion 5. The syringe portion 5 is disposed between the distal end side housing 3 and the proximal end side housing 4. These components are fixed to each other to be integrated using screws, whereby the housing 2 is formed. Alternatively, the distal end side housing 3, the proximal end side housing 4, and the syringe portion 5 may be connected to each other by a known method other than the screws. A hole 40 is formed inside the proximal end side housing 4 to extend in the axial direction thereof and serve as an internal space.

The syringe portion 5 has a containing chamber (containing portion) 50 that contains injection solution ML, formed therein. The syringe portion 5 is attached to the proximal end side housing 4 by being screwed thereto. In the attached state, the hole 40 inside the proximal end side housing 4 and the containing chamber 50 inside the syringe portion 5 form a continuous space. In this attached state, a plunger 7 makes the injection solution ML liquid tightly contained inside the containing chamber 50, and is exposed on the side of the hole 40. Here, the plunger 7 is slidably disposed within the containing chamber 50, and slides to pressurize the injection solution ML. As a result, the injection solution is injected through the injection port. The plunger 7 is formed with a rubber member having a surface coated by a thin silicone oil to be capable of smoothly sliding inside the containing chamber 50. For example, the surface of the plunger 7 may be fluorinated to improve the slidability of the plunger 7.

A piston 6 made of metal is disposed in the hole 40 in the proximal end side housing 4, and the piston 6 is held to be slidable within the hole 40. The piston 6 is generally formed in a shape of a shaft extending in the axial direction of the hole 40, and has a first end portion 6*a* that comes into contact with the plunger 7 disposed in the syringe portion 5, and a second end portion 6*b* provided on a side opposite to the first end portion 6*a* and defines a combustion chamber 41, which will be described later. An O ring 6*c* is provided around a portion of the piston 6 on the side of the second end portion 6*b*. The O ring 6*c* is configured to seal combustion products as a result of combustion of an ignition charge described later inside the combustion chamber 41, while enabling the piston 6 to smoothly slide in the hole 40.

Furthermore, in the proximal end side housing 4, an initiator 20 is disposed on a side opposite to the side to which the syringe portion 5 is attached. As illustrated in FIG. 1(*a*), the initiator 20 is provided at an end portion on the proximal end side of the housing 2. The initiator 20 closes the combustion chamber 41 formed at one end of the hole 40. The combustion chamber 41 is a space, in the hole 40, defined by the initiator 20 and the second end portion 6*b* of the piston 6. When a voltage is applied to the initiator 20, the ignition charge contained in the initiator 20 is combusted. Then, the combustion products as a result of the combustion of the ignition charge flow into the combustion chamber 41, and the pressure inside the combustion chamber 41 rises. As a result, injection energy is generated to inject the injection solution ML contained in the containing chamber 50. The initiator 20 serves as a drive unit that generates the injection energy.

Note that, examples of the ignition charge used in the injector 1 preferably include an explosive containing zirconium and potassium perchlorate (ZPP), an explosive containing titanium hydride and potassium perchlorate (THPP), an explosive containing titanium and potassium perchlorate (TiPP), an explosive containing aluminum and potassium perchlorate (APP), an explosive containing aluminum and bismuth oxide (ABO), an explosive containing aluminum and molybdenum oxide (AMO), an explosive containing aluminum and copper oxide (ACO), an explosive containing aluminum and iron oxide (AFO), or an explosive composed of a combination of a plurality of these explosives. These explosives exhibit characteristics that, although the explosives generate high-temperature and high-pressure plasma during combustion immediately after ignition, when the combustion product condenses at room temperature, that the explosives do not contain gaseous components and that the pressure generated decreases abruptly. Note that an explosive other than these may be used as the ignition charge.

Although the combustion chamber 41 illustrated in FIG. 1 contains nothing, the combustion chamber 41 may contain a gas generating agent that generates gas upon being combusted by the combustion products as a result of the combustion of the ignition charge. As one example of the gas generating agent that may be contained in the combustion chamber 41, there may be exemplified a single base smokeless explosive formed of 98 mass % of nitrocellulose, 0.8 mass % of diphenylamine, and 1.2 mass % of potassium sulfate. Further, various types of gas generating agents used in a gas generator for an air bag and a gas generator for a seat belt pretensioner may be used. When such a gas generating agent is also used, the predetermined gas generated by the combustion includes a gas component even at room temperature unlike in a case where only the ignition charge described above is used, and thus the generated pressure drops at a lower rate. The gas generating agent combusted takes a longer combustion completion time than the ignition charge. This combustion completion time of the gas generating agent can be varied by adjusting the dimensions, the size, and the surface shape in particular of the gas generating agent 41 being disposed inside the combustion chamber 41. With the amount, shape, and arrangement of the gas generating agent thus changed, the pressure generated inside the combustion chamber 41 can be appropriately adjusted.

In the injector 1 with the above described configuration, the distal end side housing 3 is attached to the syringe portion 5 by screwing. Note that the distal end side housing 3 is attached to the syringe portion 5 with a gasket 3a interposed therebetween. A nozzle portion 8 and a rim 9 are integrally formed with the distal end side housing 3. The nozzle portion 8 and the rim 9 (pressing portion) are provided to protrude from a predetermined end portion 2a, which is a predetermined end portion on the distal end side (the side of the containing chamber 50) of the housing 2. Note that the nozzle portion 8 and the rim 9 may each be provided as a component separate from the distal end side housing 3. The protruding orientation of the nozzle portion 8 and the rim 9 is parallel to the axial direction of the housing 2, but does not necessarily need to be parallel to this axis, and may be slightly inclined.

The nozzle portion 8 includes a body 8a having a diameter smaller than that on the syringe portion 5 side of the distal end side housing 3. The body 8a includes: a proximal end portion 82a that has a diameter gradually decreasing from the predetermined end portion 2a toward the distal end side along the axial direction; and a distal end portion 81a formed to be more on the distal end side than the proximal end portion 82a. As illustrated in FIG. 1(b), the diameter of the distal end portion 81a of the body 8a is denoted by D1. In the nozzle portion 8, an injection port 8b is formed at the distal end portion 81a of the body 8a. The injection solution ML pressurized by the plunger 7 flows through a flow path formed in the distal end side housing 3 and is injected from the injection port 8b. Specifically, when the pressure inside the combustion chamber 41 rises due to the combustion of the ignition charge of the initiator 20, the piston 6 slides toward the distal end side of the injector 1. Then, as the piston 6 slides, the plunger 7 presses the injection solution ML contained in the containing chamber 50. As a result, the injection solution ML flows through the flow path formed in the distal end side housing 3, to be injected from the injection port 8b toward the injection target region.

Note that one or a plurality of the injection ports 8b may be formed at the distal end portion 81a of the body 8a. When a plurality of injection ports are formed, flow paths respectively corresponding to the injection ports are formed in the body 8a of the nozzle portion 8 to make the injection solution ML fed as evenly as possible to the injection ports. Furthermore, when a plurality of injection ports are formed, the injection ports are preferably disposed at an equal interval around the center axis of the injector 1, as illustrated in FIG. 1(c).

The rim 9 is formed around the nozzle portion 8 of the distal end side housing 3. The rim 9 has a cylindrical shape protruding from the predetermined end portion 2a, and has the inner diameter denoted by d2, as illustrated in FIG. 1(b). In the present embodiment, the distance between the inner circumferential surface and the outer circumferential surface of the rim 9 is constant, that is, does not change along the axial direction. In the present embodiment, the rim 9 has an annular shape that is continuous along the circumferential direction, but the rim 9 can be formed into a plurality of independent arcuate shapes as long as the effects of the present invention described below can be obtained. In such a case, the length of the arc is set to be longer than the distance between adjacent arcs.

A predetermined gap 10 is formed between the rim 9 and the nozzle portion 8. The injector 1 according to the present invention has the gap 10 thus provided between the rim 9 and the nozzle portion 8. When the injection solution ML is injected to the injection target region of the subject, the injection target region is pressed by the rim 9, and thus a part of the injection target region enters into the gap 10. In other words, the gap 10 receives a part of the injection target region. Note that the rim 9 serves as a pressing portion that presses the injection target region. A surface of the rim 9 on the distal end side (that is, the surface that presses the injection target region as described later), and a surface of the distal end portion 8a of the nozzle portion 8 on the distal end side (that is, a surface that comes into contact with the injection target region at the time of injection) are in a positional relationship to be on the same plane in a direction orthogonal to the axial direction of the housing 2. Thus, the surfaces are in a positional relationship to be flush with each other. The positional relationship between the surface of the rim 9 on the distal end side and the surface of the distal end portion 8a of the nozzle portion 8 on the distal end side is not limited to the positional relationship to be flush with each other as described above. Thus, a configuration may be adopted in which one of the surfaces is positioned on the distal end side along the axial direction of the housing 2. Furthermore, the "positional relationship to be flush with each other" in the disclosure of the present application also encompasses positional relationships involving an offset within a range of the processing tolerance and assembly tolerance of components that are well known to those skilled in the art. In other words, the surface of the rim 9 on the distal end side and the surface of the distal end portion 8a of the nozzle portion 8 on the distal end side can be regarded as being in the positional relationship to be flush with each other, as long as the offset therebetween is within a range of tolerance in the injector 1. This will be described in detail below.

Figure 2:
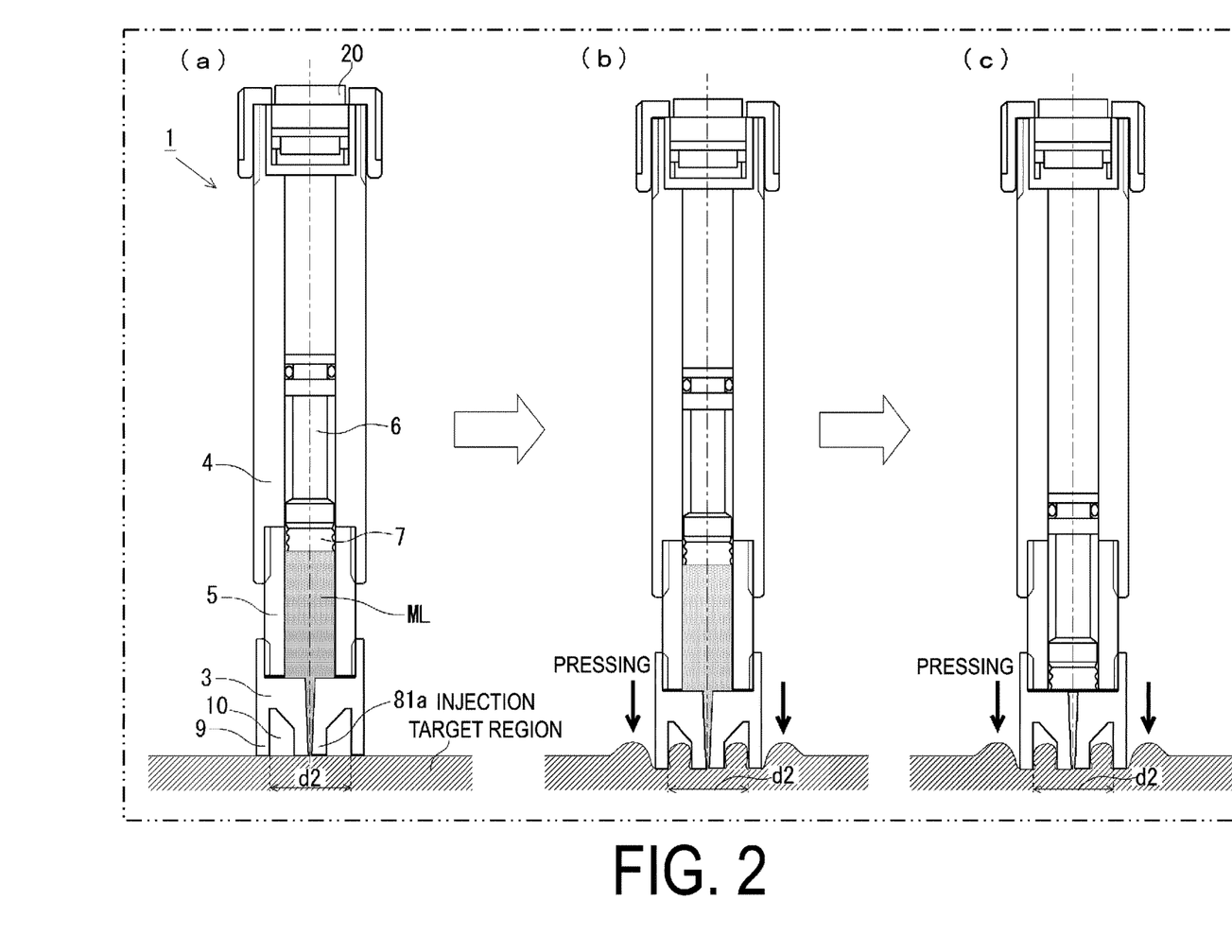
FIG. 2 is a view illustrating a contact state between an injection target region and a distal end portion of a nozzle portion at the time when injection solution is injected into the injection target region of a subject.

FIG. 2 is a view illustrating the contact state between the injection target region and the distal end portion 81a of the nozzle portion 8 at the time when the injection solution ML is injected to the injection target region of the subject. In the present invention, the injection solution ML is injected in a state where the injection target region is pressed by the rim 9. FIG. 2(a) illustrates a state in which the surface of the injection target region and the distal end portion of the rim 9 are in contact with each other (a state in which no load is applied to the injection target region). FIG. 2(b) illustrates a state in which the injection target region is pressed by the rim 9 from the state illustrated in FIG. 2(a). FIG. 2(c) illustrates a state in which the initiator 20 is actuated in the state illustrated in FIG. 2(b), and injection of the injection solution ML is completed.

As illustrated in FIG. 2(b), when the injection target region is pressed by the rim 9, a portion of the injection target region in contact with the rim 9 is depressed, and a part of the injection target region enters the gap 10. Here, if the nozzle portion 8 is not disposed inside the rim 9 that is a cylindrical member, the injection target region is likely to be raised to have an arcuate cross-sectional shape on the inner side of the rim 9. For example, when the injection target region is pressed by the rim 9 in a circular form, the injection target region is raised in a dome shape on the inner side of the rim 9. The injector 1 of the present invention has the nozzle portion 8 disposed inside the rim 9. Thus, on the inner side of the rim 9, the injection target region which would otherwise be raised in an arc shape toward the injector 1 is pressed down by the distal end portion 81a of the nozzle portion 8, and the injection target region on the inner side of the rim 9 enters the gap 10. In the injector 1 according to an embodiment of the present invention, the injection target region and the nozzle portion 8 are brought into contact with each other in this manner. Note that, in the state illustrated in FIG. 2(b), a desired contact state described later between the injection target region and the nozzle portion 8 is achieved with the gap 10 suitably receiving the injection target region in a region surrounded by the inner circumferential edge of the rim 9 having the inner diameter d2.

When a voltage is applied to the initiator 20 in the state illustrated in FIG. 2(b), the combustion products generated by the combustion of the ignition charge flow into the combustion chamber 41, and thus the pressure inside the combustion chamber 41 rises. Then, the injection solution ML is pressed by the plunger 7, to be injected from the injection port 8b toward the injection target region. As a result, the state of injector 1 illustrated in FIG. 2(c) is achieved.

Thus, in the injector 1, when the injection solution ML is injected to the injection target region of the subject, the injection solution ML is injected from the injection port 8b in a state in which the injection target region and the distal end portion 81a of the nozzle portion 8 are in contact with each other. In this process, the injection solution ML may fail to be precisely delivered to the target region of the injection target region, if an appropriate contact state fails to be achieved between the injection target region and the nozzle portion 8 or to be maintained during the injection of the injection solution ML.

In view of this, in the injector 1 according to the present invention, the nozzle portion 8 is formed to make the width of the portion of the distal end portion 81a of the nozzle portion 8 that comes into contact with the injection target region, that is, the diameter D1 of the distal end portion 81a fall within a range from 3.5 mm to 5.5 mm. Note that these values (3.5 mm and 5.5 mm) are merely target values for manufacturing, and dimensional tolerance allows the diameter D1 of the distal end portion 81a to be slightly smaller than 3.5 mm or slightly larger than 5.5 mm. The range from 3.5 mm to 5.5 mm according to the present invention does not exclude such a case (for example, cases where the diameter D1 is 3.4 mm or 5.6 mm due to manufacturing variation). Furthermore, the injector 1 according to the present invention is configured to have a ratio (hereinafter, also referred to as "gap configuration ratio") defined by dividing an inner diameter d2 of the rim 9 (i.e., the inner diameter of a portion of the distal end portion of the rim 9 that comes into contact with the injection target region) by the diameter D1 of the distal end portion 81a of the nozzle portion 8 falling within a range from 1.5 to 5.0. This enables the injection to be performed while suitably achieving and maintaining the contact state (hereinafter, also referred to as a "desired contact state") between the injection target region and the nozzle portion 8 allowing the injection solution ML to be precisely delivered to the target region of the injection target region when the injection solution ML is injected to the injection target region of the subject. This will be described on the basis of FIG. 3.

Figure 3:
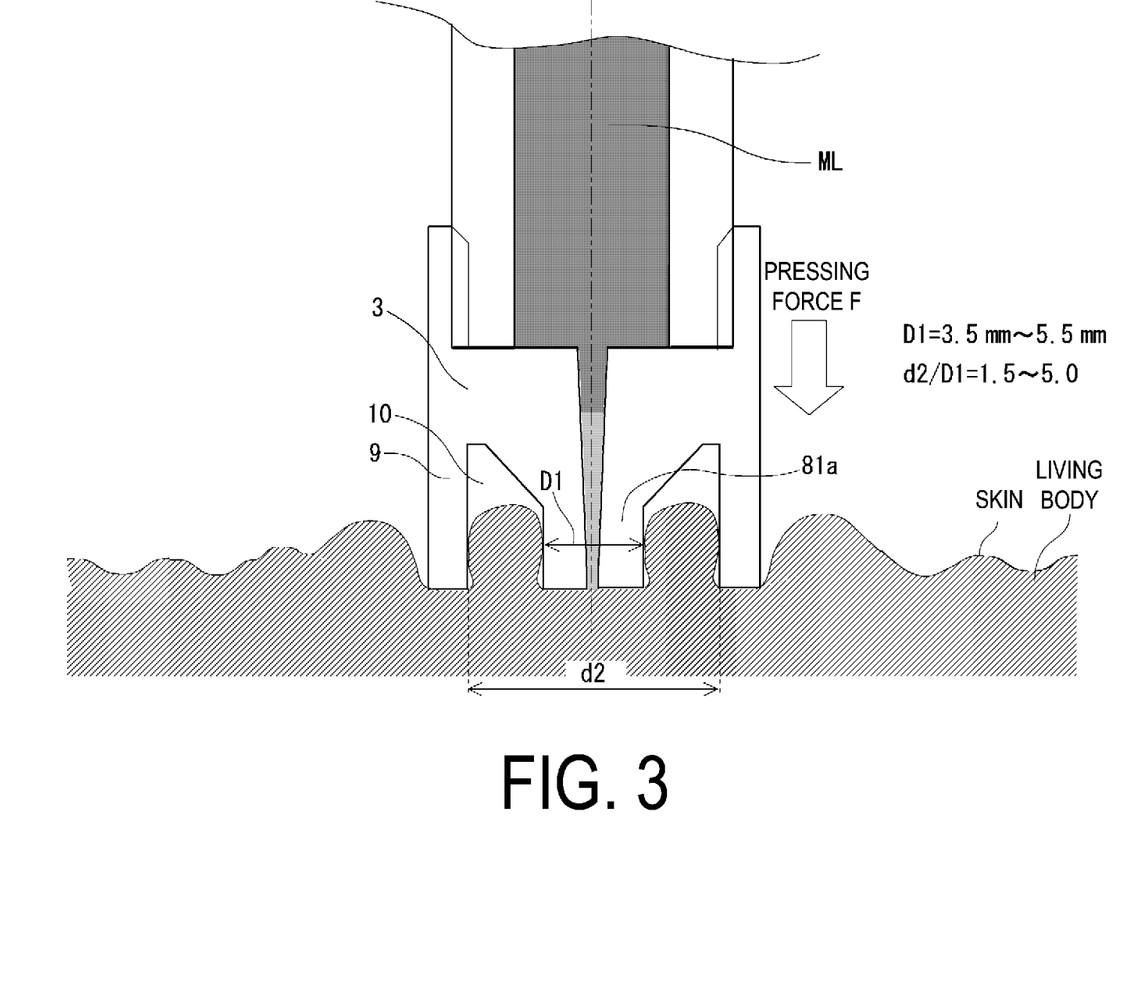
FIG. 3 is a view illustrating a contact state between the skin of an organism and the distal end portion of the nozzle portion achieved with a rim pressing the skin of the organism, under a condition where a desired contact state is achieved between the skin and the nozzle portion.

FIG. 3 illustrates a contact state between the skin of an organism and the distal end portion 81a of the nozzle portion 8 with the skin of the organism being pressed by the rim 9. Note that in the example illustrated by FIG. 3, the diameter D1 of the distal end portion 81a of the nozzle portion 8 falls within the range from 3.5 mm to 5.5 mm, and the gap configuration ratio falls within the range from 1.5 to 5.0.

Here, if the diameter D1 of the distal end portion 81a of the nozzle portion 8 is smaller than 3.5 mm, a contact area between the distal end surface of the nozzle portion 8 and the skin is relatively small. Thus, the contact state between the skin and the nozzle portion 8 is likely to change depending on a manipulation by the user or the like in a process for performing an injection operation, for example. Specifically, if the diameter D1 of the distal end portion 81a of the nozzle portion 8 is smaller than 3.5 mm, it is difficult to bring the distal end surface of the nozzle portion 8 into surface contact with the skin. Thus, the contact state between the skin and the nozzle portion 8 is difficult to stably maintain. As a result, administration of the injection solution ML to the target region of the injection target region is difficult to stably and reproducibly perform. Furthermore, as described later, the injection target region received in the gap 10 presses the outer circumferential surface of the distal end portion 81a of the nozzle portion 8. If the diameter D1 of the distal end portion 81a is smaller than 3.5 mm, the outer circumferential surface of the distal end portion 81a is less likely to be uniformly pressed. Therefore, by setting the diameter D1 of the distal end portion 81a of the nozzle portion 8 to be 3.5 mm or greater, the contact state between the skin and the nozzle portion 8 is stably maintained. In particular, the diameter D1 set to be 4.0 mm or greater enables mating with a vial adapter (ISO594 compliant product), meaning that the medication can be sucked out from a vial bottle. Thus, usability can be increased.

On the other hand, it is not preferable to set the diameter D1 to be excessively large. Specifically, if the diameter D1 of the distal end portion 81a of the nozzle portion 8 is greater than 5.5 mm, the nozzle portion 8 might hinder the blistering of skin, when the skin and the nozzle portion 8 come into contact with each other with the rim 9 pressing the skin. Furthermore, a larger diameter D1 of the distal end portion 81a of the nozzle portion 8 directly leads to a larger inner diameter d2 of the rim 9, rendering uniform pressing of the skin by the rim 9 difficult. Therefore, by setting the diameter D1 of the distal end portion 81a of the nozzle portion 8 to be 5.5 mm or less, the contact state between the skin and the nozzle portion 8 is stably maintained. In particular, the diameter D1 set to be 4.5 mm or less enables mating with a vial adapter (ISO594 compliant product), meaning that the medication can be sucked out from a vial bottle. Thus, usability can be increased. This will be described later in conjunction with the description of the gap configuration ratio.

Figure 4A:
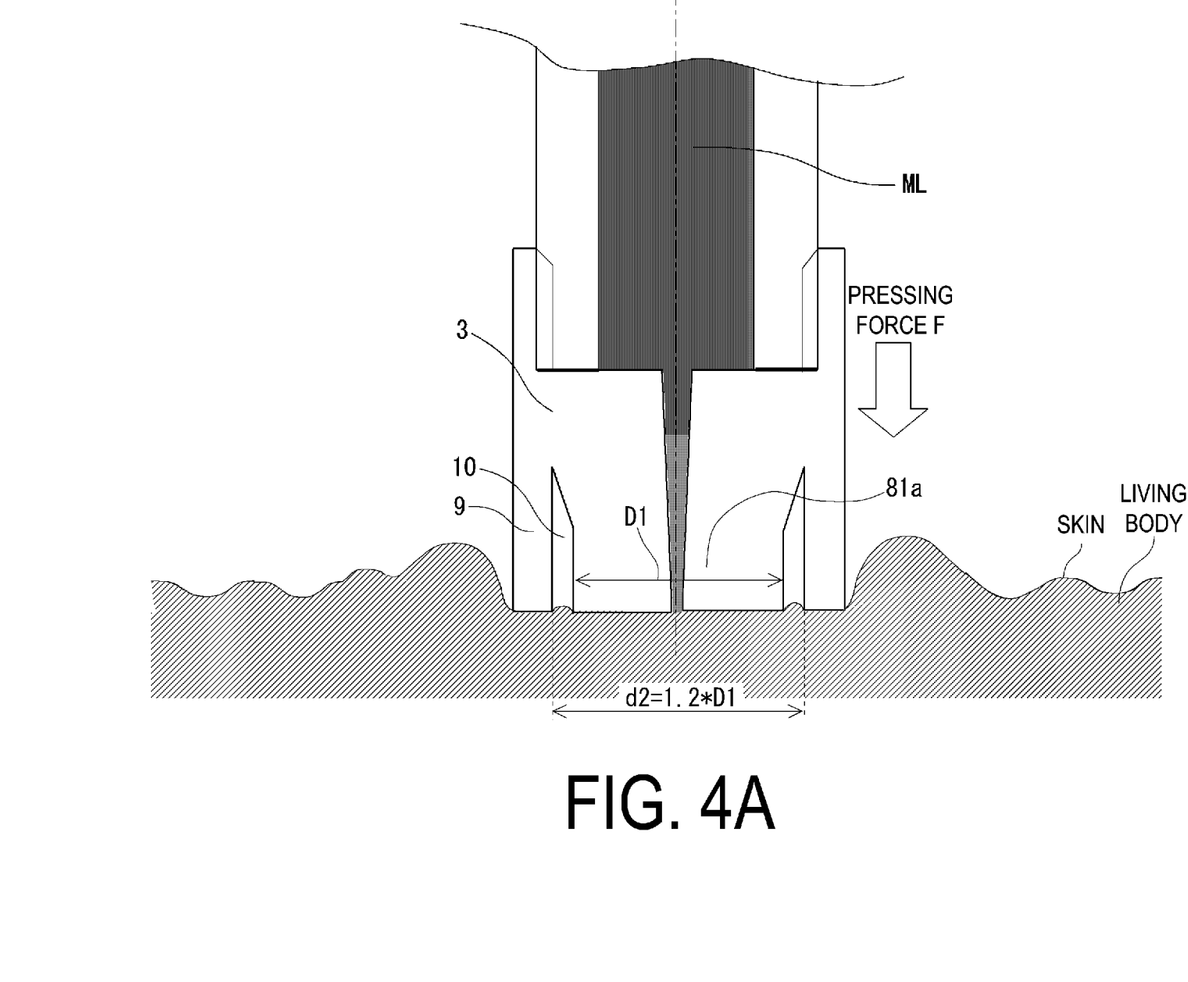
FIG. 4A is a view illustrating an example of a contact state between the skin of the organism and the distal end portion of the nozzle portion achieved with the rim pressing the skin of the organism, in a case where a gap configuration ratio is smaller than 1.5.

FIG. 4A is a view illustrating an example of a contact state between the skin of the organism and the distal end portion 81a of the nozzle portion 8 achieved with the rim 9 pressing the skin of the organism, in a case where the gap configuration ratio is smaller than 1.5 (and is 1.2, for example). The gap configuration ratio smaller than 1.5 results in the gap 10 being narrow as illustrated in FIG. 4A, rendering a space for the skin to deform to be risen on the inner side of the rim 9 difficult to secure. As a result, the above deformation of the skin of the inner side of the rim 9 is hindered, and thus the desired contact state between the skin and the nozzle portion 8 cannot be achieved.

Figure 4B:
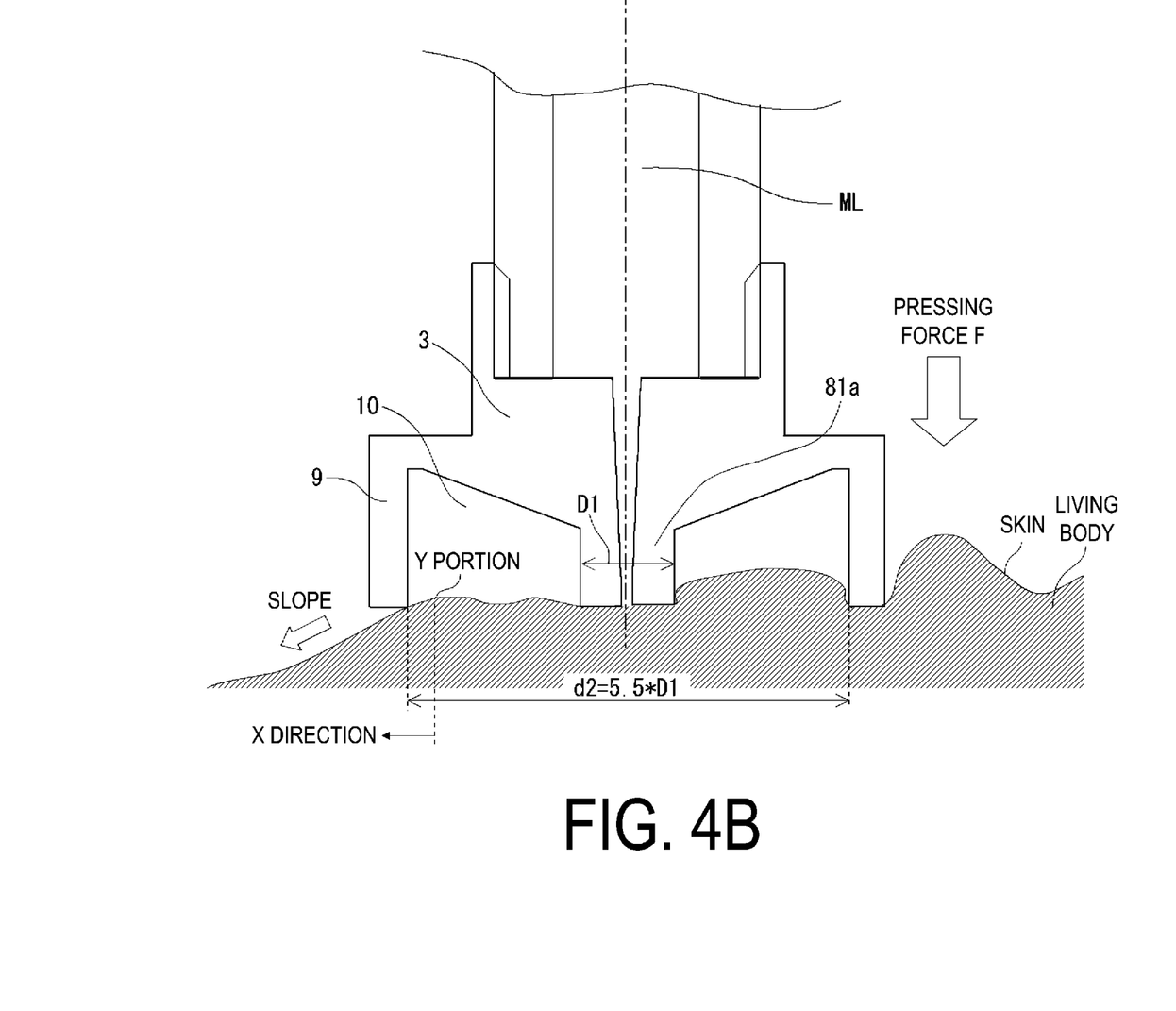
FIG. 4B is a view illustrating an example of a contact state between the skin of the organism and the distal end portion of the nozzle portion achieved with the rim pressing the skin of the organism, in a case where a gap configuration ratio is greater than 0.5.

FIG. 4B is a view illustrating a contact state between the skin of the organism and the distal end portion 81a of the nozzle portion 8 achieved with the rim 9 pressing the skin of the organism in a case where the gap configuration ratio is greater than 5.0 (and is 5.5, for example). The gap configuration ratio greater than 5.0 results in the inner diameter d2 of the rim 9 being relatively large, rendering uniform pressing of the skin by the rim 9 difficult. This is because, in this case, pressing by the rim 9 on the skin is implemented over a relatively large area, to involve a higher risk of being affected by a predetermined shape of the organism. FIG. 4B illustrates an example where the organism is shaped to have a slope from a Y portion, close to a portion where the injection solution ML is administered, toward the side opposite to the side where the injector 1 is provided, in an X direction. In this case, the skin that is more on the X direction side than the Y portion cannot be sufficiently pressed by the rim 9. Thus, the gap configuration ratio greater than 5.0 renders uniform pressing of the skin by the rim 9 difficult. As a result, the skin becomes difficult to be raised in the gap 10, resulting in a failure to establish the desired contact state between the skin and the nozzle portion 8.

As described above, with the gap configuration ratio less than 1.5 or greater than 5.0, the desired contact state cannot be achieved between the injection target region and the nozzle portion 8. Also, when the inner diameter d2 of the rim 9 is set to be large due to the diameter D1 of the distal end portion 81a of the nozzle portion 8 set to be large, the skin is less likely to be uniformly pressed by the rim 9 as described above. Thus, the desired contact state cannot be achieved between the injection target region and the nozzle portion 8.

On the other hand, in the example illustrated in FIG. 3, the gap configuration ratio of 1.5 or greater results in a relatively wide gap 10. Thus, a space for the skin to deform to be raised is secured on the inner side of the rim 9. Further, the gap configuration ratio of 5.0 or less facilitates uniform pressing of the skin by the rim 9. Thus, the skin can be suitable raised in the gap 10. With the above configuration, the injection target region deformed to be raised due to the pressing by the rim 9 can be suitably received in the gap 10. Preferably, the gap configuration ratio is set to be 2.0 or greater and 4.5 or less. Furthermore, the diameter D1 of the distal end portion 81a of the nozzle portion 8 is set to be 3.5 or greater and 5.5 mm or less, thus allowing the distal end surface of the nozzle portion 8 and the skin to be stably in contact with each other. Preferably, the diameter D1 is 4.0 mm or greater and 4.5 mm or less. Then, the injection target region and the nozzle portion 8 are brought into contact with each other with the injection target region received in the gap 10 as described above pressed against the distal end portion 81a of the nozzle portion 8. Thus, the desired contact state is achieved between the injection target region and the nozzle portion 8.

Furthermore, with the injector 1 according to the present invention, such a desired contact state can be stably achieved. This is because the above-described geometric shapes of the rim 9 and the distal end portion 81a of the nozzle portion 8 have a dominant impact on the mode of deformation of the injection target region on the inner side of the rim 9. This means that the contact state between the injection target region and the nozzle portion 8 is less likely to vary due to a difference in the manipulation by the user and the like.

The injection target region received in the gap 10 presses the outer circumferential surface of the distal end portion 81a and surrounds the distal end portion 81a of the nozzle portion 8. As a result, the nozzle portion 8 is fixed by the injection target region, whereby maintaining of the desired contact state is facilitated.

With the injector 1 described above, the desired contact state can be appropriately achieved and maintained between the injection target region and the nozzle portion 8. As a result, the administration of the injection solution ML to the target region of the injection target region can be performed accurately, stably, and reproducibly.

Modified Example 1 of Embodiment

Figure 5:
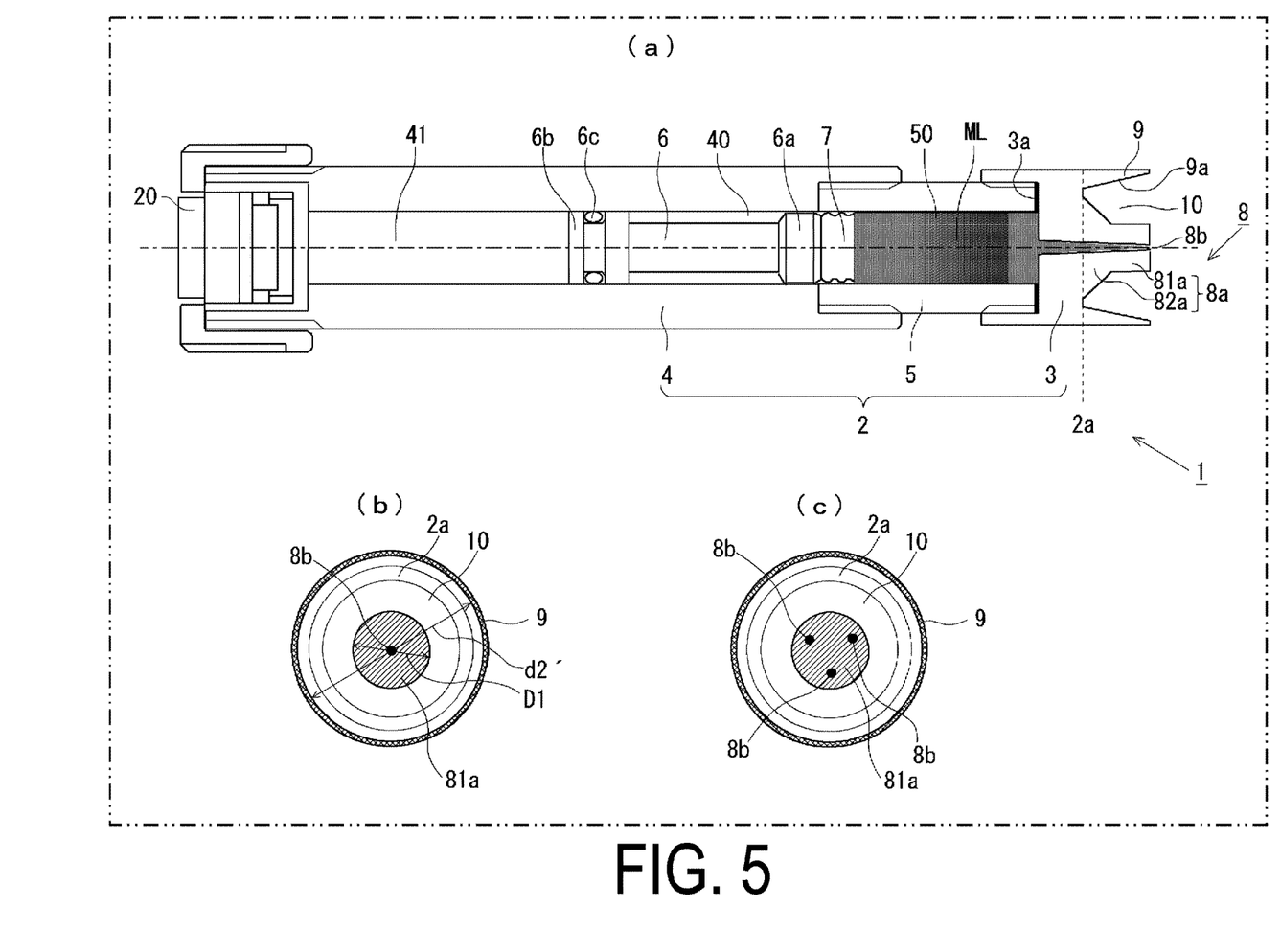
FIG. 5 is a view illustrating a schematic configuration of an injector according to Modified Example 1 of the embodiment of the present invention.

Next, Modified Example 1 of the embodiment described above will be described on the basis of FIGS. 5 and 6. Note that, in the present modified example, detailed description for components substantially the same as those in the embodiment described above will be omitted. FIG. 5(*a*) is a cross-sectional view of an injector 1 according to the present modified example. FIGS. 5(*b*) and (*c*) are views of the injector 1 according to the present modified example as viewed from the distal end side.

As illustrated in FIG. 5(*a*), in the injector 1 according to the present modified example, the rim 9 has a tapered portion 9*a*. Specifically, the tapered portion 9*a* is formed on the inner circumferential surface of the cylindrical rim 9. With the tapered portion 9*a*, the distance between the inner circumferential surface and the outer circumferential surface of the rim 9 gradually decreases toward the distal end side along the axial direction. A tapered portion may be formed on the outer circumferential surface of the cylindrical rim 9 to make the distance between the inner circumferential surface and the outer circumferential surface of the rim 9 gradually decrease toward the distal end side along the axial direction.

In the present modified example, as illustrated in FIG. 5(*b*), the inner diameter of the distal end surface of the rim 9 is denoted by d2'. Also in this case, the gap configuration ratio defined by dividing the inner diameter d2' at the distal end surface of the rim 9 (the inner diameter of the portion of the distal end portion of the rim 9 to be in contact with the injection target region) by the diameter D1 of the distal end portion 81a of the nozzle portion 8 falls within the range from 1.5 to 5.0. Also with such an injector 1, a desired contact state can be suitably achieved and maintained between the injection target region and the nozzle portion 8. This will be described on the basis of FIG. 6.

Figure 6:
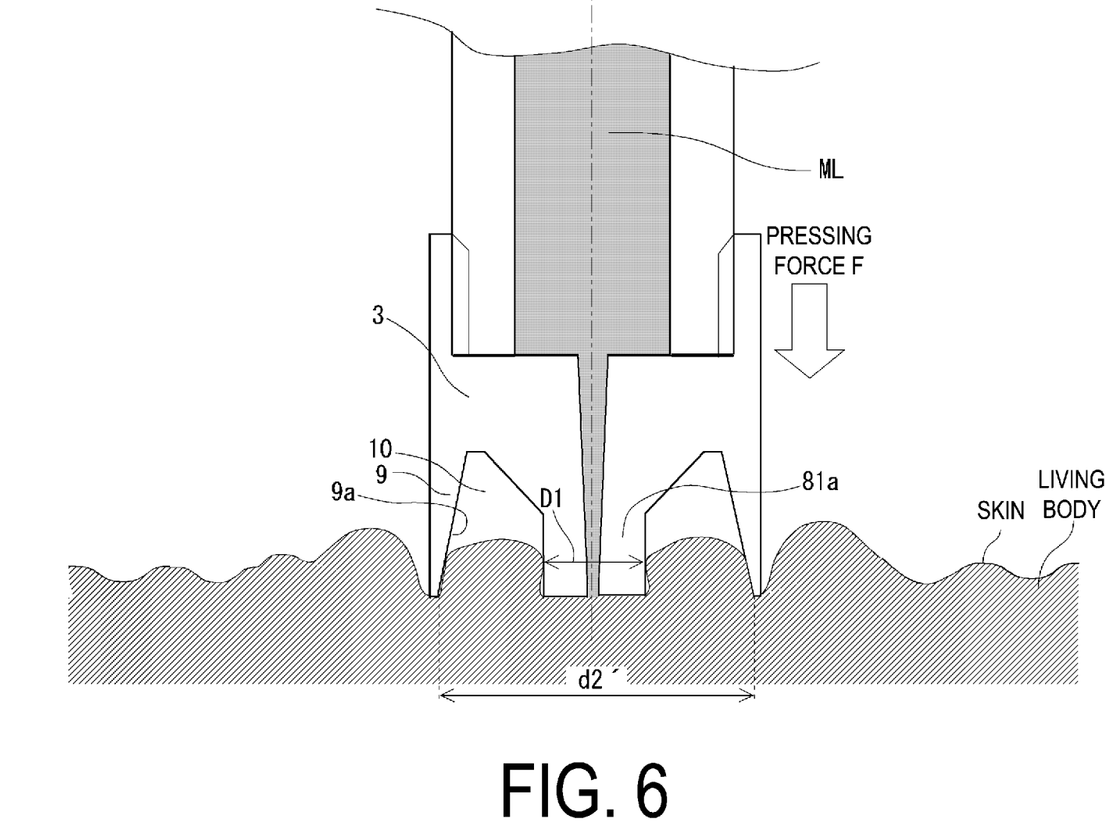
FIG. 6 illustrates a contact state between the skin of an organism and the distal end portion of the nozzle portion with the skin of the organism being pressed by the rim, according to Modified Example 1.

FIG. 6 illustrates an example of a contact state between the skin of an organism and the distal end portion 81a of the nozzle portion 8 with the skin of the organism being pressed by the rim 9 as in FIG. 3. With the injector 1 according to the present modified example, the rim 9 is pressed relatively deeper into the skin as illustrated in FIG. 6. This is because with a thinner distal end portion of the rim 9 (smaller area of the distal end surface of the rim 9), a load applied to the skin surface by the distal end surface of the rim 9 is more concentrated under the same pressing force. Also by pressing the skin in this way, the skin deformed to be risen by the pressing is suitably received in the gap 10, and the desired contact state is achieved between the skin and the nozzle portion 8.

With such an injector 1, a desired contact state can be stably achieved and maintained between the injection target region and the nozzle portion 8. This is because the rim 9 pressed relatively deeper into the injection target region facilitates stable maintaining of the pressing state of the rim 9 against the injection target region. With this configuration, for example, even when tilting or the like of the injector 1 occurs in the process of performing the injection operation, the injection target region deformed as described above on the inner side of the rim 9 can be favorably maintained in the deformed mode.

Thus, the desired contact state is suitably achieved and maintained between the injection target region and the nozzle portion 8, whereby the administration of the injection solution ML to the target region of the injection target region can be accurately, stably, and reproducibly performed.

Modified Example 2 of Embodiment

Figure 7:
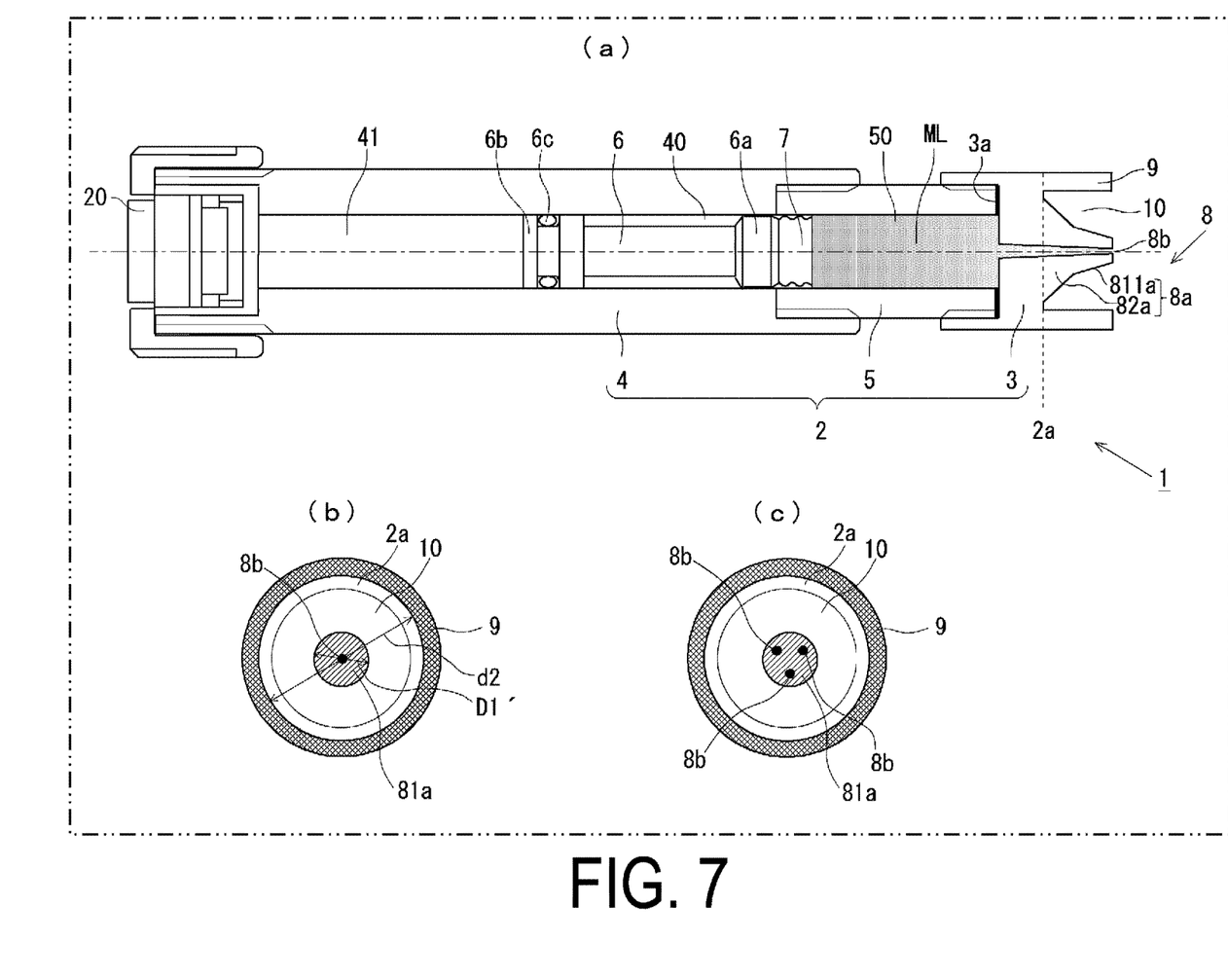
FIG. 7 is a view illustrating a schematic configuration of an injector according to Modified Example 2 of the embodiment of the present invention.

Next, Modified Example 2 of the embodiment described above will be described on the basis of FIGS. 7 and 8. Note that, in the present modified example, detailed description for components substantially the same as those in the embodiment described above will be omitted. FIG. 7(*a*) is a cross-sectional view of an injector 1 according to the present modified example. FIGS. 7(*b*) and (*c*) are views of the injector 1 according to the present modified example as viewed from the distal end side.

In the injector 1 according to the above described embodiment, the body 8*a* of the nozzle portion 8 includes the proximal end portion 82*a* having a diameter gradually decreasing from the predetermined end portion 2*a* toward the distal end side along the axial direction, and the distal end portion 81*a* that is formed to be more on the distal end side of the proximal end portion 82*a* and has a constant diameter over the entire length. On the other hand, in the injector 1 according to the present modified example, the body 8*a* of the nozzle portion 8 includes the proximal end portion 82*a* similar to that in the injector 1 according to the above described embodiment, and a distal end portion 811*a* that is formed to be more on the distal end side than the proximal end portion 82*a* and has a diameter gradually decreasing toward the distal end side along the axial direction.

In the present modified example, as illustrated in FIG. 7(*b*), the diameter of the distal end surface of the distal end portion 811*a* of the nozzle portion 8 is denoted by D1'. Also in this case, the gap configuration ratio defined by dividing the inner diameter d2 of the rim 9 by the diameter D1' falls within the range from 1.5 to 5.0. Also with such an injector 1, a desired contact state can be suitably achieved and maintained between the injection target region and the nozzle portion 8. This will be described on the basis of FIG. 8.

Figure 8:
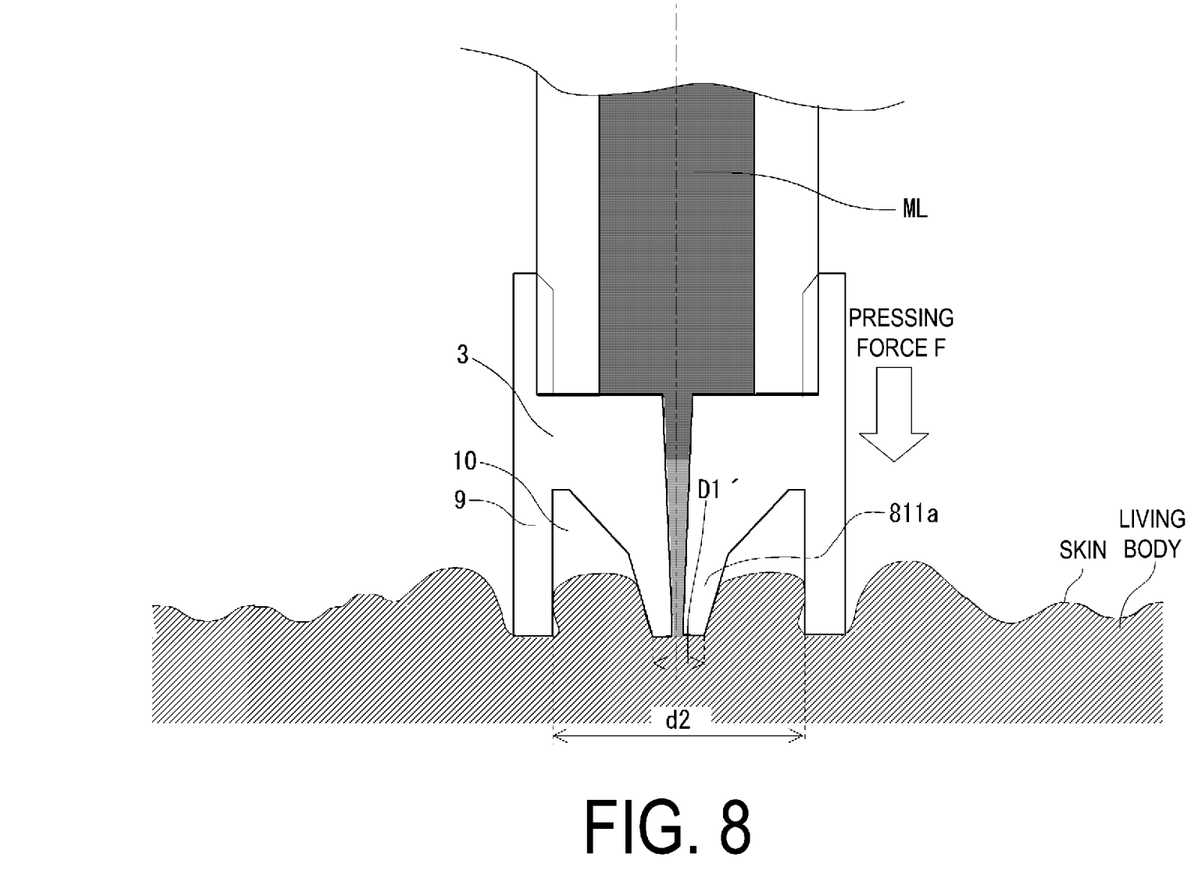
FIG. 8 illustrates a contact state between the skin of an organism and the distal end portion of the nozzle portion with the skin of the organism being pressed by the rim, according to Modified Example 2.

FIG. 8 illustrates an example of a contact state between the skin of an organism and the distal end portion 811*a* of the nozzle portion 8 with the skin of the organism being pressed by the rim 9 as in FIG. 3. With the injector 1 according to the present modified example, as illustrated in FIG. 8, the distal end portion 811*a* of the nozzle portion 8 can be easily pressed into the skin. As a result, the nozzle portion 8 is easily fixed by the injection target region surrounding the outer circumferential surface of the distal end portion 811*a*, and the desired contact state is easily maintained between the injection target region and the nozzle portion 8.

Thus, the desired contact state is suitably achieved and maintained between the injection target region and the nozzle portion 8, whereby the administration of the injection solution ML to the target region of the injection target region can be accurately, stably, and reproducibly performed.

EXAMPLE 1

Now, the experimental conditions and experimental results will be described below for a first administration experiment performed on a pig organism using the injector 1 according to the present invention. Note that in the present example, the injector 1 was operated in a state where the containing chamber 50 of the injector 1 is filled with 100 μL of ink, and an abdomen region of the pig is pressed by the rim 9 of the injector 1. Then, after the entire volume of the ink has been discharged from the injection port 8*b* of the nozzle portion 8 by the operation of the injector 1, the injector 1 was separated from the skin surface and the affected area surface was observed.

Furthermore, the skin of the affected area was cut out and the cross-section of the affected area was observed.
Experimental Conditions
Pressing Force The pressing force by the rim 9 on the skin of the abdominal region of the pig was set to be 4 to 6 N.
Diameter D1 of distal end portion 81*a* of nozzle portion 8

As described above, the diameter D1 of the distal end portion 81*a* of the nozzle portion 8 less than 3.5 mm renders the stable maintaining of the contact state between the skin and the nozzle portion 8 difficult. The diameter D1 greater than 5.5 mm results in a risk of the nozzle portion 8 hindering blistering of the skin. In view of this, the diameter D1 of the distal end portion 81*a* of the nozzle portion 8 was set to be 3.5 mm, 4.5 mm, and 5.5 mm, which fall within the range from 3.5 mm to 5.5 mm.

When the inner diameter d2 of the rim 9 is 8.5 mm, D1=3.5 mm results in d2/D1=2.4, D1=4.5 mm results in d2/D1=1.9, and D1=5.5 mm results in d2/D1=1.5.

When the inner diameter d2 of the rim 9 is 11.5 mm, D1=3.5 mm results in d2/D1=3.3, D1=4.5 mm results in d2/D1=2.6, and D1=5.5 mm results in d2/D1=2.1.

When the inner diameter d2 of the rim 9 is 14.5 mm, D1=3.5 mm results in d2/D1=4.1, D1=4.5 mm results in d2/D1=3.2, and D1=5.5 mm results in d2/D1=2.6.
Experimental Results Table 1 below shows the experimental results of observing the surface and the cross section of the affected area, with the gap configuration ratio d2/D1 set to be 1.2, 1.5, 3.0, 5.0, and 6.0. Note that "liquid leakage" in the experimental results indicates whether the ink discharged from the injector 1 has leaked out on the skin instead of being administered into the skin of the pig. Whether the liquid leakage has occurred was determined through observation of the surface of the affected area. The "administration depth" indicates a portion inside the pig organism to which the ink discharged from the injector 1 has reached. The administration depth was determined through observation of the cross section of the affected area.

TABLE 1

| Result | d2/D1 | | | | |
|---|---|---|---|---|---|
| | 1.2 | 1.5 | 3.0 | 5.0 | 6.0 |
| Liquid leakage | Slight leakage | No leakage | No leakage | No leakage | Slight leakage |
| Administration depth | Intradermal to subcutaneous | Intradermal to subcutaneous | Intradermal to subcutaneous | Intradermal to subcutaneous | Intradermal to subcutaneous |

When d2/D1=1.2

Through the observation of the surface of the affected area, slight leakage of liquid was confirmed. This should be due to the failure to achieve the desired contact state between the skin and the nozzle portion 8, as a result of the space for the skin to deform to be raised on the inner side of the rim 9 being difficult to secure as described above with reference to FIG. 4A. It has also been confirmed through the observation of the cross section of the affected area that the ink injected into the skin was distributed from the intradermal to subcutaneous in the pig organism.

When d2/D1=1.5, 3.0, 5.0

Through the observation of the surface of the affected area, no leakage of liquid was confirmed. Thus, the ink discharged from the injector 1 was entirely injected into the skin of the pig. It has also been confirmed through the observation of the cross section of the affected area that the ink was distributed from the intradermal to subcutaneous in the pig organism.

When d2/D1=6.0

Through the observation of the surface of the affected area, occurrence of slight leakage of liquid was confirmed. This should be due to the failure to achieve the desired contact state between the skin and the nozzle portion 8, as a result of the skin being difficult to be raised in the gap 10, as described above with reference to FIG. 4B. It has also been confirmed through the observation of the cross section of the affected area that the ink injected into the skin was distributed from the intradermal to subcutaneous in the pig organism.

The results described above indicates that the nozzle portion 8 is in the appropriate contact state with the surface of the skin of the pig when d2/D1=1.5 to 5.0.

EXAMPLE 2

Now, the experimental conditions and experimental results will be described below for a second administration experiment performed on a pig organism using the injector 1 according to the present invention. Note that also in the present example, the injector 1 was operated in a state where the containing chamber 50 of the injector 1 is filled with 100 μL of ink, and an abdomen region of the pig is pressed by the rim 9 of the injector 1, as in the first administration experiment. Under this condition, the injection performance of the injector 1 was investigated while changing the positional relationship between the distal end surface of the rim 9 and the distal end surface of the distal end portion 81a of the nozzle portion 8, in a direction orthogonal to the axial direction of the housing 2.

Pressing Force

The pressing force by the rim 9 on the skin of the abdominal region of the pig was set to be 4 to 6 N.

D1 and d2/D1

In any of the experiments, D1 falls within the range from 3.5 mm to 5.5 mm, and d2/D1 falls with the range from 1.5 to 5.0.

Positional relationship between distal end surface of distal end portion 81a of nozzle portion 8 and distal end surface of rim 9.

Three patterns were prepared that are different from each other in the positional relationship between the distal end surface of the distal end portion 81a of the nozzle portion 8 and the distal end surface of the rim 9. Specifically, the prepared patterns for the pressing force include: a pattern in which the distal end surface of the distal end portion 81a of the nozzle distal end portion 8 is positioned more on the rear side than the distal end surface of the rim 9 by 0.5 mm (a pattern with protrusion allowance of the distal end portion 81a being 0.5 mm); a pattern in which the distal end surface of the distal end portion 81a of the nozzle distal end portion 8 and the distal end surface of the rim 9 are flush with each other (a pattern with protrusion allowance of the distal end portion 81a being 0 mm); and a pattern in which the distal end surface of the distal end portion 81a of the nozzle distal end portion 8 is positioned more on the forward side than the distal end surface of the rim 9 by 0.5 mm (a pattern with protrusion allowance of the distal end portion 81a being 0.5 mm).

Table 2 below shows the experimental results based on the conditions described above.

TABLE 2

| d2 [mm] | 9 | | | 12 | | | 15 | | |
|---|---|---|---|---|---|---|---|---|---|
| D1 [mm] | 3.5 | | | 3.5 | | | 3.5 | | |
| d2/D1 | 2.6 | | | 3.4 | | | 4.3 | | |
| Offset allowance of distal end portion 81a [mm] | −0.5 | 0 | 0.5 | −0.5 | 0 | 0.5 | −0.5 | 0 | 0.5 |
| Average value of injection rate | 86% | 94% | 78% | 91% | 94% | 91% | 88% | 93% | 88% |
| Standard error | 7% | 3% | 6% | 5% | 2% | 5% | 6% | 6% | 5% |

The injection rate is defined as a percentage value as a result of dividing the weight of the medication injected into the skin by the weight of the medication actually discharged from the inside of the syringe when the medication is administrated to the skin of the pig. The injection rate of 93% or higher was achieved with the distal end surface of the distal end portion 81a of the nozzle portion 8 positioned to be flush with the distal end surface of the rim 9. In contrast, the injection rate slightly dropped from that in the flush case, with the injector 1 having the configuration in which the distal end surface of the distal end portion 81a of the nozzle portion 8 offset forward or rearward with from the distal end surface of the rim 9 by 0.5 mm. This indicates that the injection rate can be improved with the injector 1 having the distal end surface of the distal end portion 81a of the nozzle portion 8 and the distal end surface of the rim 9 in a positional relationship to be flush with each other.

Other Embodiments

With the injector 1 according to the present invention, in the field of regenerative medicine for humans, as described in JP 2008-206477 A, in accordance with an implanted part and a purpose of re-cellularization, a cell that can be determined appropriately by a person skilled in the art, for example, an endothelial cell, an endothelial precursor cell, a myeloid cell, a preosteoblast cell, a cartilagenous cell, a fibroblast cell, a skin cell, a muscle cell, a liver cell, a kidney cell, an intestinal cell, a stem cell, or any other cells that may be considered in a field of regenerative medicine can be injected using the injector 1. Specifically, liquid (cell suspension) including the cell described above is contained in the containing chamber 50 and pressurized. As a result, a predetermined cell is injected and implanted to an implant target region.

Furthermore, the injector 1 according to the present invention can be used for delivery of DNA or the like as described in JP 2007-525192 T. In this case, the use of the injector 1 according to the present invention should be advantageous over a case where the delivery is implemented using a needle, because calls, scaffold tissue, and the like are less affected by the use of the injector 1.

Furthermore, the injector 1 according to the present invention is suitably used to deliver various genes, cancer suppressor cells, lipid envelopes, and the like, or administering antigen genes to enhance immunity to pathogens. Furthermore, the injector 1 can be used in various types of disease treatment fields (in the fields described in JP 2008-508881 T, JP 2010-503616 T, and the like), the field of immunotherapy (the field described in JP 2005-523679 T), and the like. Thus, there is no intention to limit the applicable field of the injector 1.

REFERENCE SIGNS LIST

1 Injector
2 Housing
3 Distal end side housing
4 Proximal end side housing
5 Syringe portion
6 Piston
7 Plunger
8 Nozzle portion
8a Body
81a Distal end portion
8b Injection port
9 Rim
10 Gap
20 Initiator
50 Containing chamber

The invention claimed is:

1. A needleless injector configured to inject an injection intended substance to an injection target region without using an injection needle, by injecting the injection intended substance in a state where the injection target region is pressed, the needleless injector comprising:
  a containing portion that is provided in a housing of the needleless injector, and is configured to contain the injection intended substance;
  a drive unit that is provided in the housing, and is configured to generate injection energy for injecting the injection intended substance contained in the containing portion;
  a nozzle portion that is provided to protrude from a predetermined end portion as a predetermined end portion of the housing on a side of the containing portion, has an injection port formed for injecting toward the injection target region, the injection intended substance provided with the injection energy generated by the drive unit, and is configured to have a distal end portion coming into contact with the injection target region when the injection intended substance is injected from the injection port; and
  a pressing portion that is provided to protrude from the predetermined end portion and to have a cylindrical shape to surround the nozzle portion with a predetermined gap formed between the nozzle portion and the pressing portion, and is configured to have a distal end portion coming into contact with the injection target region when the injection intended substance is injected from the injection port, wherein
  the nozzle portion is formed to have a portion of the distal end portion that comes into contact with the injection target region and has a width (a) falling within a range from 3.5 mm to 5.5 mm,
  a ratio (b/a) defined by an inner diameter (b) of a portion of the distal end portion of the pressing portion that comes into contact with the injection target region by the width (a) of the portion of the distal end portion of the nozzle portion that comes into contact with the injection target region falls within a range from 2.0 to 4.5, and
  a part of the injection target region is received in the predetermined gap when the pressing portion presses the injection target region.

2. The needleless injector according to claim 1, wherein the pressing portion has a tapered shape to have a distance between an inner circumferential surface and an outer circumferential surface of the pressing portion gradually decreasing toward a distal end side along an axial direction.

3. The needleless injector according to claim 1, wherein the nozzle portion is formed to have a width gradually decreasing toward the distal end portion.

4. The needleless injector according to claim 1, wherein the nozzle portion has a distal end surface formed to be positioned on a same plane as a distal end surface of the pressing portion in a direction orthogonal to an axial direction of the housing.

* * * * *